(12) United States Patent
Teshigawara et al.

(10) Patent No.: US 8,373,131 B2
(45) Date of Patent: Feb. 12, 2013

(54) NUCLEAR MEDICINE IMAGING APPARATUS AND ANALYZING SYSTEM

(75) Inventors: Manabu Teshigawara, Otawara (JP); Takuzo Takayama, Utsunomiya (JP); Yuuji Yanagida, Otawara (JP); Takaya Umehara, Kuki (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/586,949

(22) Filed: Aug. 16, 2012

(65) Prior Publication Data

US 2012/0312996 A1     Dec. 13, 2012

Related U.S. Application Data

(63) Continuation of application No. PCT/JP2011/067792, filed on Aug. 3, 2011.

(30) Foreign Application Priority Data

Aug. 9, 2010 (JP) .................. 2010-178603

(51) Int. Cl.
*G01T 1/164* (2006.01)
(52) U.S. Cl. .................. 250/363.03
(58) Field of Classification Search ......... 250/362, 250/363.01–363.1; 378/98.8
See application file for complete search history.

(56) References Cited

U.S. PATENT DOCUMENTS 5,353,262 A * 10/1994 Yakymyshyn et al. ....... 367/149
6,528,985 B1    3/2003 Greuel et al.
6,694,172 B1    2/2004 Gagnon et al.
2008/0053230 A1    3/2008 Katsura et al.

FOREIGN PATENT DOCUMENTS

| JP | 01-292799 | 11/1989 |
| JP | 2001-194346 | 7/2001 |
| JP | 2004-532998 | 10/2004 |
| JP | 2005-114376 | 4/2005 |
| JP | 2006-052982 | 2/2006 |
| JP | 2008-244380 | 10/2008 |
| WO | WO 2006/075615 | 7/2006 |

OTHER PUBLICATIONS

Japan Industries Association of Radiological Systems, "Medical Image/Radiological Equipment Hand Book", published by Nago Bijutsu Insatsu Kabushiki Kaisha, 2001 (with partial English translation).
International Search Report issued on Aug. 30, 2011 for PCT/JP2011/067792 filed on Aug. 3, 2011 (with English translation of categories).
International Written Opinion issued on Aug. 30, 2011 for PCT/JP2011/067792 filed on Aug. 3, 2011.

* cited by examiner

*Primary Examiner* — Kiho Kim
(74) *Attorney, Agent, or Firm* — Oblon, Spivak, McClelland, Maier & Neustadt, L.L.P.

(57) ABSTRACT

A PET apparatus includes an optical coupling detachment testing unit. In one example, the optical coupling detachment testing unit inputs an electric signal to a piezoelectric element or the like adhered to a detector module and generates a sound wave within the detector module. Further, the optical coupling detachment testing unit detects the sound wave propagated within the detector module and performs a frequency analysis on the detected sound wave. Subsequently, as a result of the analysis, the optical coupling detachment testing unit detects whether an optical coupling detachment has occurred by looking for a frequency distribution specific to a surface having an optical coupling detachment and/or comparing a frequency distribution with another frequency distribution from a previous test.

7 Claims, 7 Drawing Sheets

| MODULE ID | SCINTILLATOR NUMBER (P) | ENERGY VALUE (E) | DETECTION TIME (T) |
|---|---|---|---|
| D1 | P11 | E11 | T11 |
| | P12 | E12 | T12 |
| | P13 | E13 | T13 |
| | ⋮ | ⋮ | ⋮ |

| MODULE ID | SCINTILLATOR NUMBER (P) | ENERGY VALUE (E) | DETECTION TIME (T) |
|---|---|---|---|
| D2 | P21 | E21 | T21 |
| | P22 | E22 | T22 |
| | P23 | E23 | T23 |
| | ⋮ | ⋮ | ⋮ |

| MODULE ID | SCINTILLATOR NUMBER (P) | ENERGY VALUE (E) | DETECTION TIME (T) |
|---|---|---|---|
| D3 | P31 | E31 | T31 |
| | P32 | E32 | T32 |
| | P33 | E33 | T33 |
| | ⋮ | ⋮ | ⋮ |

| COINCIDENCE NUMBER | SCINTILLATOR NUMBER (P) | ENERGY VALUE (E) | DETECTION TIME (T) | SCINTILLATOR NUMBER (P) | ENERGY VALUE (E) | DETECTION TIME (T) |
|---|---|---|---|---|---|---|
| 1 | P11 | E11 | T11 | P22 | E22 | T22 |
| 2 | P12 | E12 | T12 | P32 | E32 | T32 |
| 3 | P13 | E13 | T13 | P33 | E33 | T33 |
| ... | ... | ... | ... | ... | ... | ... |

NUCLEAR MEDICINE IMAGING APPARATUS AND ANALYZING SYSTEM

CROSS-REFERENCE TO RELATED APPLICATIONS

This application is a continuation of PCT international application Ser. No. PCT/JP2011/067792 filed on Aug. 3, 2011 which designates the United States, and which claims the benefit of priority from Japanese Patent Application No. 2010-178603, filed on Aug. 9, 2010; the entire contents of which are incorporated herein by reference.

FIELD

Exemplary embodiments relate to a nuclear medicine imaging apparatus and an analyzing system.

BACKGROUND

As a nuclear medicine imaging apparatus, Positron Emission computed Tomography (PET) apparatuses are conventionally known. A PET apparatus generates, for example, a function image of a tissue in a human body. More specifically, to perform an image taking process using a PET apparatus, a subject is first dosed with a radiopharmaceutical labeled with a positron emitting nuclide. After that, the positron emitting nuclide that is selectively taken into a body tissue within the subject releases positrons, and the released positrons are coupled with electrons and annihilated. At this time, the positrons release a pair of gamma rays in substantially opposite directions. The PET apparatus detects the gamma rays by using a detector arranged in a ring formation so as to surround the subject and generates simultaneous count information (hereinafter, a "coincidence list") from the detection result. Further, the PET apparatus performs a reconstructing process through a back-projection process by using the generated coincidence list and generates a PET image.

In this situation, the detector for the PET apparatus includes a scintillator, a photomultiplier tube, and a light guide. An optical coupling between the scintillator and the light guide and an optical coupling between the light guide and the photomultiplier tube are important factors in the performance of the detector. For this reason, materials having similar refractive indexes are usually used at the optical coupling surfaces so as to prevent reflection and scattering of the light. Also, the materials are adhered to each other while ensuring that no air layer or the like is involved.

Generally speaking, however, the optical coupling mentioned above has a possibility of experiencing a detachment due to vibrations during a transport, deteriorations in the course of time, and the like. It is also difficult to visually check for occurrence of optical coupling detachments, because radiating light onto the detector has a possibility of disturbing the mechanical property of the detector. For this reason, a method by which it is possible to check for optical coupling detachments in a nondestructive manner has been in demand.

BRIEF DESCRIPTION OF THE DRAWINGS

FIG. 5 is a drawing of an example of a coincidence list stored in a coincidence list storage unit according to the first embodiment.

DETAILED DESCRIPTION

Figure 1:
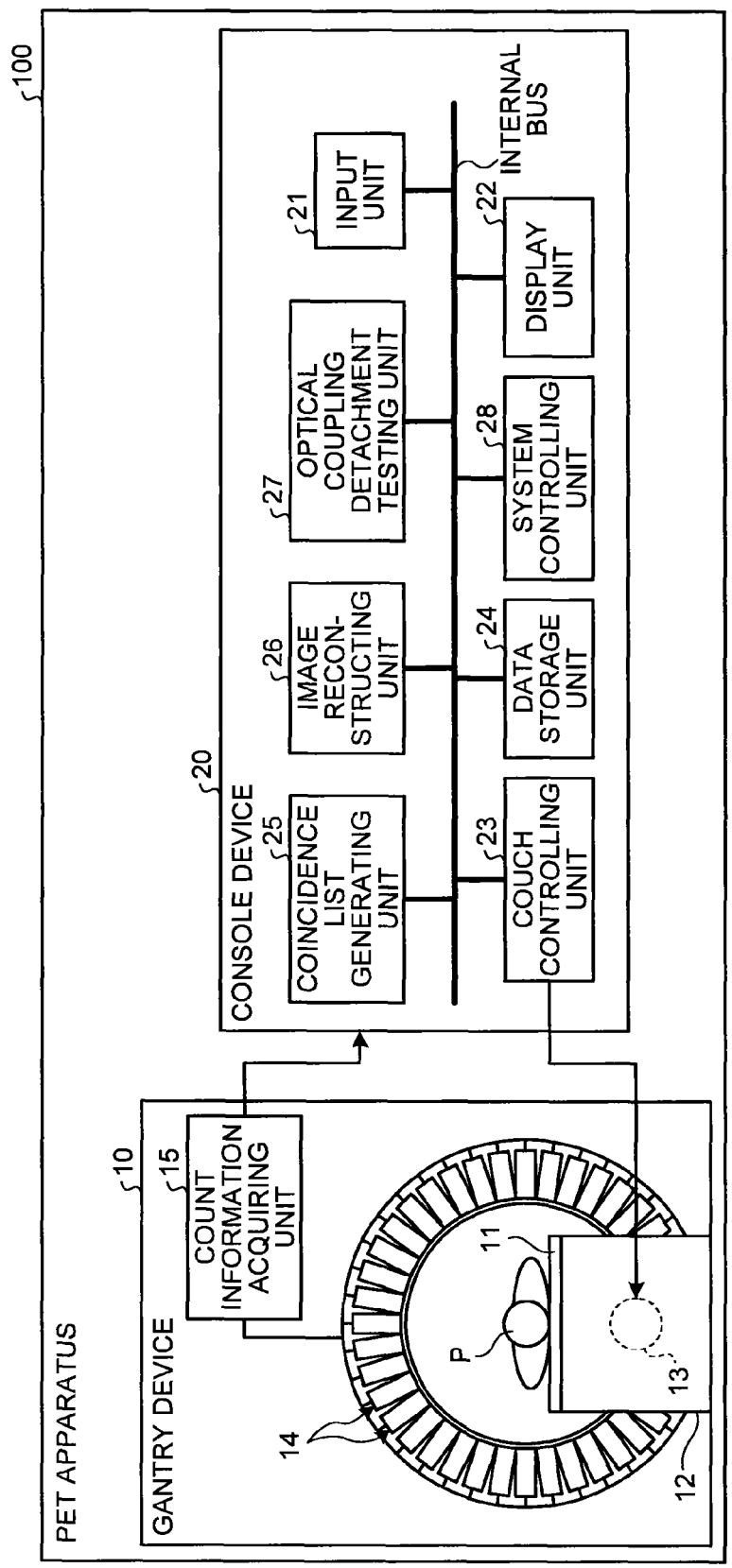
FIG. 1 is a block diagram of a PET apparatus according to a first embodiment.

A nuclear medicine imaging apparatus according to an embodiment includes a detector, a sound wave generating unit, a sound wave detecting unit, and an analyzing unit. The detector is configured to detect radiation emitted from a subject. The sound wave generating unit is configured to input an electric signal to the detector and to generate a sound wave within the detector. The sound wave detecting unit is configured to detect the sound wave propagated within the detector. The analyzing unit is configured to analyze the sound wave detected by the sound wave detecting unit.

An analyzing system according to an embodiment includes a nuclear medicine imaging apparatus, a receiving unit, and an analyzing unit. The nuclear medicine imaging apparatus according to an embodiment includes a detector, a sound wave generating unit, a sound wave detecting unit, and a transmitting unit. The detector is configured to detect radiation emitted from a subject. The sound wave generating unit is configured to input an electric signal to the detector and to generate a sound wave within the detector. The sound wave detecting unit is configured to detect the sound wave propagated within the detector. The transmitting unit is configured to transmit a signal related to the sound wave detected by the sound wave detecting unit. The receiving unit is configured to receive, via a network, the signal related to the sound wave transmitted from the transmitting unit. The analyzing unit is configured to analyze the sound wave based on the received signal related to the sound wave.

In the following sections, examples of a nuclear medicine imaging apparatus and an analyzing system according to exemplary embodiments will be explained. First, a PET apparatus 100 according to a first embodiment will be explained, together with modification examples thereof. After that, an analyzing system according to a second embodiment will be explained. The analyzing system according to the second embodiment includes, as explained later, a PET apparatus 150 and an analyzing apparatus 200.

First Embodiment

The PET apparatus 100 according to the first embodiment realizes an optical coupling detachment test by using sound waves. More specifically, the PET apparatus 100 according to the first embodiment inputs an electric signal to a piezoelectric element or the like adhered to a detector module and generates a sound wave within the detector module. Further, the PET apparatus 100 according to the first embodiment detects the sound wave propagated within the detector module and performs a frequency analysis on the detected sound wave. Further, as a result of the analysis, the PET apparatus 100 according to the first embodiment detects whether an optical coupling detachment has occurred by looking for a frequency distribution specific to a surface having an optical coupling detachment and/or comparing a frequency distribution with another frequency distribution from a previous test.

The optical coupling detachment test is primarily realized by an optical coupling detachment testing unit 27, which is explained later. In the following sections, a configuration of the PET apparatus 100 according to the first embodiment will be explained first, before the test performed by the optical coupling detachment testing unit 27 is explained in detail.

A Configuration of the PET Apparatus 100 According to the First Embodiment

First, a configuration of the PET apparatus 100 according to the first embodiment will be explained with reference to FIGS. 1 to 5. FIG. 1 is a block diagram of the PET apparatus 100 according to the first embodiment. As shown in FIG. 1, the PET apparatus 100 according to the first embodiment includes a gantry device 10 and a console device.

The gantry device 10 detects a pair of gamma rays emitted from a positron and acquires count information based on the detection result. As shown in FIG. 1, the gantry device 10 includes a couchtop 11, a couch 12, a couch driving unit 13, detector modules 14, and a count information acquiring unit 15. As shown in FIG. 1, the gantry device 10 has a hollow serving as an image-taking opening.

The couchtop 11 is a bed on which a subject P lies down and is positioned on top of the couch 12. Under the control of a couch controlling unit 23 (explained later), the couch driving unit 13 moves the couchtop 11. For example, by moving the couchtop 11, the couch driving unit 13 moves the subject P into the space inside the image-taking opening of the gantry device 10.

The detector modules 14 detect the gamma rays emitted from the subject P. As shown in FIG. 1, within the gantry device 10, the plurality of detector modules 14 are arranged in a ring formation so as to surround the subject P.

Figure 2A:
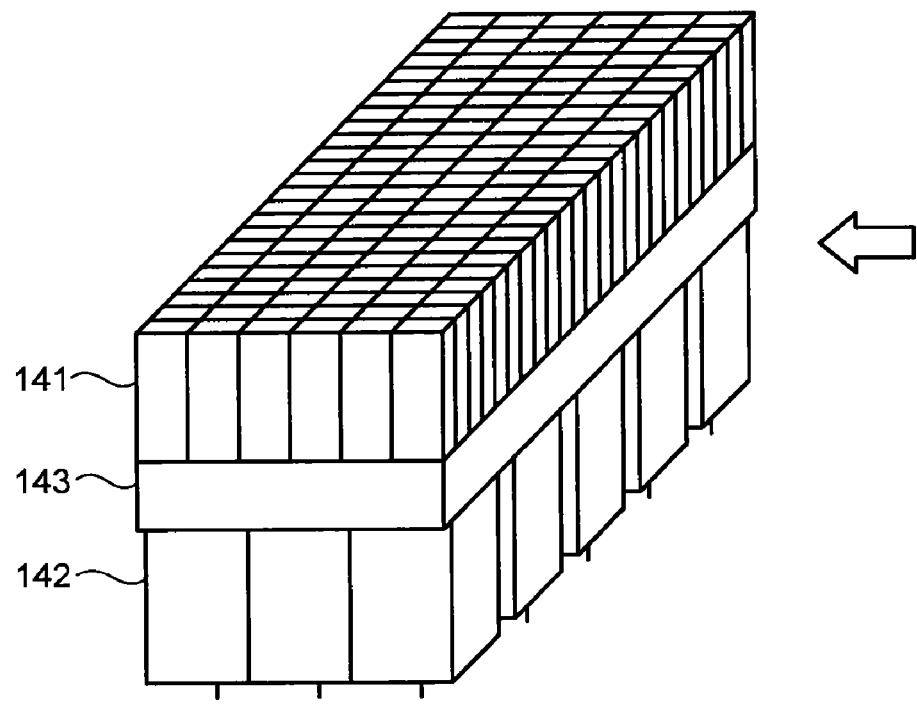
FIG. 2A is a drawing for explaining a detector module according to the first embodiment.
Figure 2B:
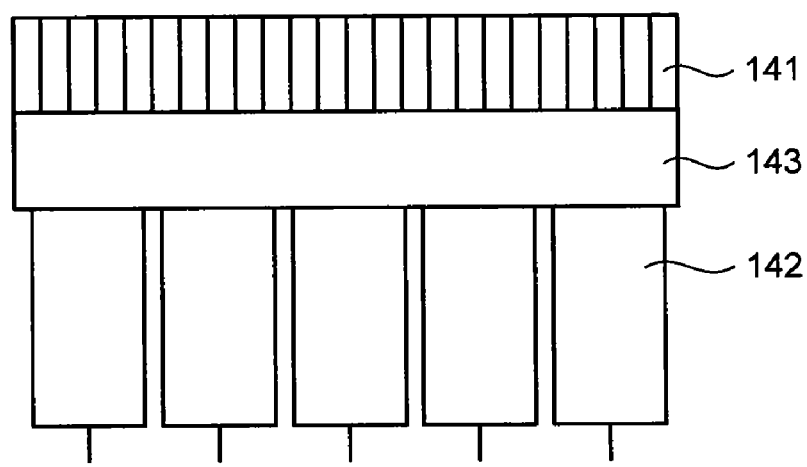
FIG. 2B is another drawing for explaining the detector module according to the first embodiment.

FIGS. 2A and 2B are drawings for explaining the detector modules 14 according to the first embodiment. As shown in FIG. 2A, each of the detector modules 14 is an Anger-type detector that uses a photon counting method. Each of the detector modules 14 includes scintillators 141, photomultiplier tubes (may be referred to as "PMTs") 142, and a light guide 143. FIG. 2B depicts the detector module 14 viewed from the direction of the arrow shown in FIG. 2A.

The scintillators 141 convert the gamma rays that are emitted from the subject P and entered therein into visible light and output the visible light (hereinafter, "scintillation light") resulting from the conversion. The scintillators 141 are configured with scintillator crystals of, for example, NaI (sodium iodide), BGO (bismuth germanate), LYSO (lutetium yttrium oxyorthosilicate), LSO (lutetium oxyorthosilicate), LGSO (lutetium gadolinium oxyorthosilicate), or the like. As shown in FIG. 2A, the scintillators 141 are arranged in a two-dimensional formation. Further, the photomultiplier tubes 142 multiply the scintillation light output from the scintillators 141 and covert the multiplied scintillation light into an electric signal. As shown in FIG. 2A, the plurality of photomultiplier tubes 142 are provided. The light guide 143 transfers the scintillation light output from the scintillator 141 to the photomultiplier tubes 142. The light guide 143 is configured by using, for example, a plastic material having an excellent light transmitting characteristic.

Each of the photomultiplier tubes 142 includes a photocathode that receives the scintillation light and generates photoelectrons; multiple stages of dynodes that create electric fields for accelerating the generated photoelectrons; and an anode from which electrons flow out. The electrons emitted from the photocathode due to the photoelectric effect are accelerated toward a dynode and collide with the surface of the dynode, so as to knock out additional electrons. When this phenomenon is repeated at the multiple stages of dynodes, the number of electrons is multiplied in the manner of an avalanche so that the number of electrons reaches as many as approximately 1 million at the anode. In this example, the gain factor of the photomultiplier tube 142 is 1 million times. To cause this multiplication utilizing the avalanche phenomenon, a voltage of 1000 volts or higher is usually applied to between the dynodes and the anode.

In this manner, the detector modules 14 detect the gamma rays emitted from the subject P, by converting the gamma rays emitted from the subject P into the scintillation light by using the scintillators 141 and further converting the converted scintillation light into the electric signal by using the photomultiplier tubes 142.

Returning to the description of FIG. 1, the count information acquiring unit 15 acquires count information based on the detection result obtained by the detector modules 14. More specifically, the count information acquiring unit 15 acquires, for each of the detector modules 14, a detection position of a gamma ray that has entered the detector module 14, an energy value of the gamma ray at the time when the gamma ray enters the detector module 14, and a detection time of the gamma ray that has entered the detector module 14. The count information acquiring unit 15 transmits the acquired count information to a console device 20.

First, the count information acquiring unit 15 performs an Anger-type position calculating process to acquire the detection positions based on the detection result obtained by the detector modules 14. More specifically, the count information acquiring unit 15 identifies some of the photomultiplier tubes 142 that converted the scintillation light having been output from the scintillators 141 into an electric signal mutually at the same time. Further, the count information acquiring unit 15 determines scintillator numbers (P) indicating the positions of the scintillators 141 which the gamma rays entered, by calculating the position of the center of gravity while using the positions of the identified photomultiplier tubes 142 and the energy values of the gamma rays corresponding to the strengths of the electric signals. If the photomultiplier tubes 142 are position-detecting-type photomultiplier tubes, the photomultiplier tubes 142 may acquire the detection positions.

Further, by calculating the integral of the strengths of the electric signals output by the photomultiplier tubes 142, the count information acquiring unit 15 determines the energy values (E) of the gamma rays that entered the detector modules 14. Also, the count information acquiring unit 15 acquires the detection times (T) at which the gamma rays were detected by the detector modules 14. For example, the count information acquiring unit 15 acquires the detection times (T) with a level of precision in the unit of $10^{-12}$ seconds (pico seconds). Each of the detection times (T) may be expressed as an absolute time or as a time period that has elapsed since the start of the image taking process, for example. The count information acquiring unit 15 acquires, as the count information, the scintillator numbers (P), the energy values (E), and the detection times (T) in this manner.

The console device 20 receives an operation performed on the PET apparatus 100 by an operator, controls a PET image taking process, and reconstructs a PET image by using the count information acquired by the gantry device 10. Also, the console device 20 performs an optical coupling detachment test. More specifically, as shown in FIG. 1, the console device 20 includes an input unit 21, a display unit 22, the couch controlling unit 23, a data storage unit 24, a coincidence list generating unit 25, an image reconstructing unit 26, the optical coupling detachment testing unit 27, and a system controlling unit 28. The functional units included in the console device 20 are connected to one another via an internal bus.

The input unit 21 is configured with a mouse and/or a keyboard used by the operator of the PET apparatus 100 for inputting various types of instructions and various types of settings and is configured so as to transfer the input various instructions and settings to the system controlling unit 28. For example, the input unit 21 is used for inputting an instruction to execute the optical coupling detachment test. The display unit 22 is a monitor or the like referenced by the operator. Under the control of the system controlling unit 28, the display unit 22 displays PET images and results of the analysis in the optical coupling detachment test, and also, displays a Graphical User Interface (GUI) for receiving the various types of instructions and the various types of settings from the operator. The couch controlling unit 23 controls the couch driving unit 13.

Figures 3, 4:
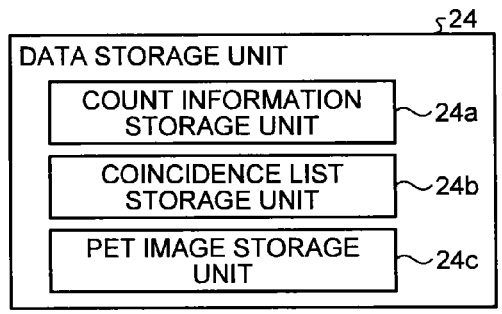
FIG. 3 is a drawing for explaining a data storage unit according to the first embodiment.
FIG. 4 is a drawing of an example of count information stored in a count information storage unit according to the first embodiment.

The data storage unit 24 stores therein various types of data used in the PET apparatus 100. FIG. 3 is a drawing for explaining the data storage unit 24 according to the first embodiment. As shown in FIG. 3, the data storage unit 24 includes a count information storage unit 24a, a coincidence list storage unit 24b, and a PET image storage unit 24c. The data storage unit 24 is realized with, for example, a semiconductor memory element such as a Random Access Memory (RAM) or a flash memory, a hard disk, or an optical disk.

The count information storage unit 24a stores therein the count information for each of the detector modules 14 acquired by the count information acquiring unit 15. More specifically, the count information storage unit 24a stores therein the count information for each of the detector modules 14 transmitted from the count information acquiring unit 15. Further, the count information stored in the count information storage unit 24a is used for processes performed by the coincidence list generating unit 25. The count information stored in the count information storage unit 24a may be deleted or may be stored for a predetermined period of time after being used for the processes performed by the coincidence list generating unit 25.

FIG. 4 is a drawing of an example of the count information stored in the count information storage unit 24a according to the first embodiment. As shown in FIG. 4, the count information storage unit 24a stores therein the scintillator numbers (P), the energy values (E), and the detection times (T), in correspondence with modules IDs each identifying a different one of the detection modules 14.

The coincidence list storage unit 24b stores therein the coincidence list generated by the coincidence list generating unit 25. More specifically, the coincidence list storage unit 24b stores the coincidence list therein, as a result of the coincidence list generating unit 25 storing the coincidence list into the coincidence list storage unit 24b. Further, the coincidence list stored in the coincidence list storage unit 24b is used for processes performed by the image reconstructing unit 26. The coincidence list stored in the coincidence list storage unit 24b may be deleted or may be stored for a predetermined period of time after being used for the processes performed by the image reconstructing unit 26.

FIG. 5 is a drawing of an example of the coincidence list stored in the coincidence list storage unit 24b according to the first embodiment. As shown in FIG. 5, the coincidence list storage unit 24b stores therein sets of count information in correspondence with coincidence numbers.

The PET image storage unit 24c stores therein the PET image reconstructed by the image reconstructing unit 26. More specifically, the PET image storage unit 24c stores the PET image therein as a result of the image reconstructing unit 26 storing the PET image into the PET image storage unit 24c. Further, the PET image stored in the PET image storage unit 24c is displayed on the display unit 22 by the system controlling unit 28.

Returning to the description of FIG. 1, the coincidence list generating unit 25 generates the coincidence list by using the count information acquired by the count information acquiring unit 15. More specifically, the coincidence list generating unit 25 reads the count information stored in the count information storage unit 24a and searches for a set of pieces of count information representing a pair of gamma rays emitted from a positron that are counted at the same time, based on the energy values and the detection times. Further, the coincidence list generating unit 25 generates the set of pieces of count information found in the search into the coincidence list and stores the generated coincidence list into the coincidence list storage unit 24b.

For example, the coincidence list generating unit 25 generates the coincidence list based on a coincidence list generating condition input by the operator. In the coincidence list generating condition, an energy window range and a time window range are specified. For example, the coincidence list generating unit 25 generates the coincidence list, based on an energy window range of "350-550 keV" and a time window range of "600 pico seconds".

For example, the coincidence list generating unit 25 refers to the energy values (E) and the detection times (T) shown in FIG. 4, by referring to the count information storage unit 24a. Further, the coincidence list generating unit 25 searches for a set of pieces of count information of which the difference in the detection times (T) is within the time window range of "600 pico seconds", and also, of which the energy values (E) are both within the energy window range of "350-550 keV", from among the detection modules 14. Further, when the coincidence list generating unit 25 finds in the search a set "P11, E11, T11" and another set "P22, E22, T22" as the sets satisfying the coincidence list generating condition, the coincidence list generating unit 25 generates these sets into the coincidence list and stores the generated coincidence list into the coincidence list storage unit 24b, as shown in FIG. 5.

The image reconstructing unit 26 reconstructs the PET image. More specifically, the image reconstructing unit 26 reconstructs the PET image by reading the coincidence list stored in the coincidence list storage unit 24b as projection data (sinogram data) and performing a back-projection process on the read projection data. Further, the image reconstructing unit 26 stores the reconstructed PET image into the PET image storage unit 24c.

The optical coupling detachment testing unit 27 realizes, in the PET apparatus 100, the optical coupling detachment test by using the sound waves. For example, when the input unit 21 receives an input of an instruction to execute an optical coupling detachment test at the time of an installation of the PET apparatus 100 or the like, the optical coupling detachment testing unit 27 performs a series of optical coupling detachment testing processes. Further, for example, the optical coupling detachment testing unit 27 performs the series of optical coupling detachment testing processes in a predetermined periodical cycle such as once in twenty-four hours or once a week. The optical coupling detachment testing processes will be explained in detail later.

The system controlling unit 28 exercises overall control of the PET apparatus 100 by controlling the gantry device 10 and the console device 20. For example, the system controlling unit 28 controls image taking processes performed by the PET apparatus 100.

The functional units described above such as the coincidence list generating unit 25, the image reconstructing unit 26, the optical coupling detachment testing unit 27, and the system controlling unit 28 are configured by using an integrated circuit such as an Application Specific Integrated Circuit (ASIC) or a Field Programmable Gate Array (FPGA) or an electronic circuit such as a Central Processing Unit (CPU) or a Micro Processing Unit (MPU).

The Optical Coupling Detachment Test According to the First Embodiment

Figure 6:
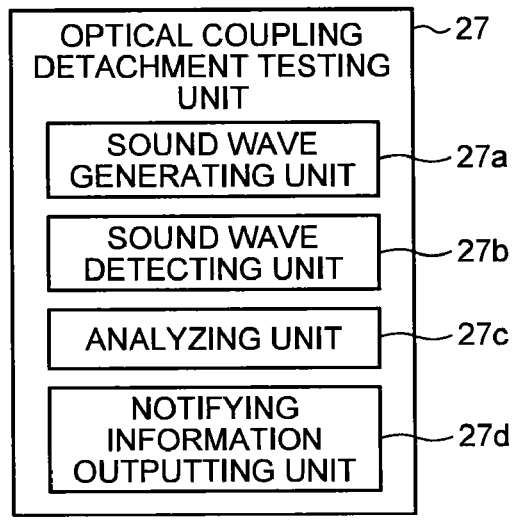
FIG. 6 is a block diagram of an optical coupling detachment testing unit according to the first embodiment.
Figure 7:
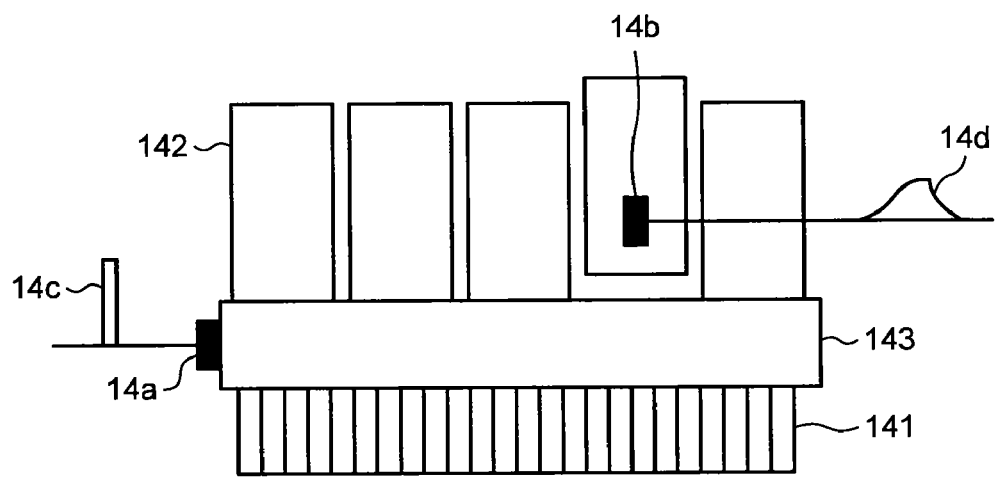
FIG. 7 is a drawing for explaining a test according to the first embodiment.
Figure 8:
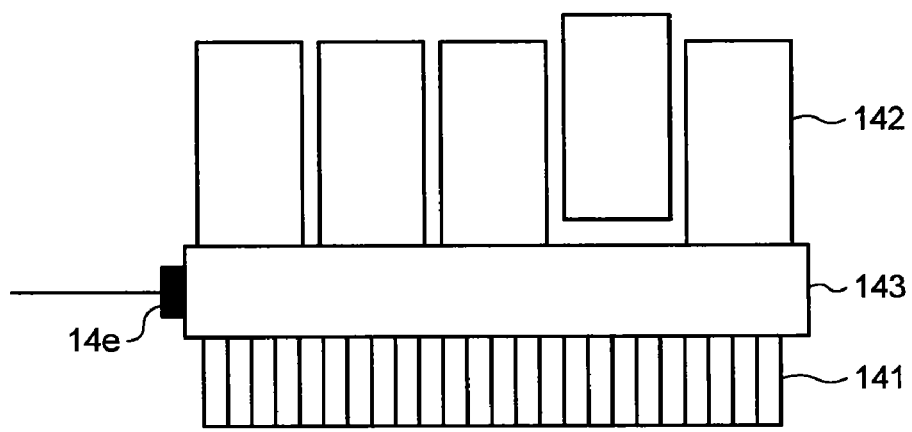
FIG. 8 is a drawing for explaining a modification example of the test according to the first embodiment.
Figure 9:
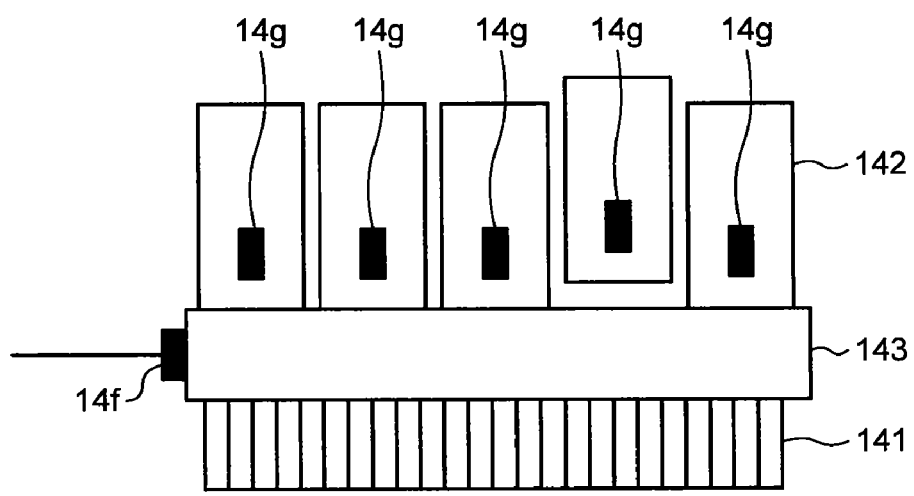
FIG. 9 is a drawing for explaining another modification example of the test according to the first embodiment.

Next, the optical coupling detachment testing unit 27 according to the first embodiment will be explained, with reference to FIGS. 6 to 9. FIG. 6 is a block diagram of the optical coupling detachment testing unit according to the first embodiment. FIG. 7 is a drawing for explaining a test according to the first embodiment. FIGS. 8 and 9 are drawings for explaining modification examples of the test according to the first embodiment.

As shown in FIG. 6, the optical coupling detachment testing unit 27 according to the first embodiment includes a sound wave generating unit 27a, a sound wave detecting unit 27b, an analyzing unit 27c, and a notifying information outputting unit 27d. Also, as shown in FIG. 7, each of the detector modules 14 according to the first embodiment is configured so that a piezoelectric element 14a is adhered to the light guide 143, and also, another piezoelectric element 14b is adhered to a predetermined one of the photomultiplier tubes 142. Further, in the example shown in FIG. 7, an optical coupling detachment has occurred between the light guide 143 and the photomultiplier tube 142 positioned second from the right among the five photomultiplier tubes 142 shown.

In the first embodiment, the example is explained in which the piezoelectric elements are adhered to the light guide 143 and to the predetermined one of the photomultiplier tubes 142; however, as explained below, the features disclosed herein are not limited to this example. Further, although the example in which the "piezoelectric elements" are adhered is explained in the first embodiment, the features disclosed herein are not limited to this example. It is possible to arbitrary select any element as long as the element is usable in the generation and the detection of the sound wave.

The sound wave generating unit 27a inputs the electric signal to each of the detector modules 14 and generates a sound wave within the detector module 14. More specifically, the sound wave generating unit 27a inputs the electric signal to the piezoelectric element 14a adhered to the light guide 143 in each of the detector modules 14 and generates the sound wave within the detector module 14.

In this situation, the sound wave generating unit 27a according to the first embodiment inputs a pulse signal (14c in FIG. 7) as the electric signal. The reason is that a pulse signal is suitable for generating a sound wave having a wide frequency band. That is to say, it is desirable if the sound wave generated for the purpose of testing for optical coupling detachments between the scintillators 141 and the light guide 143 and optical coupling detachments between the light guide 143 and the photomultiplier tubes 142 has a frequency that resonates with all of the scintillators 141, the photomultiplier tubes 142, and the light guide 143. In other words, it is desirable to generate a sound wave having a wide frequency band. For this reason, the sound wave generating unit 27a according to the first embodiment is configured so as to input, in particular, a pulse signal. The features disclosed herein are not limited to using the pulse signal. It is possible to use an electric signal other than the pulse signal.

Further, as shown in FIG. 7, the sound wave generating unit 27a according to the first embodiment inputs the electric signal to the piezoelectric element 14a adhered to the light guide 143. In other words, because the purpose is to test for optical coupling detachments between the scintillators 141 and the light guide 143 and optical coupling detachments between the light guide 143 and the photomultiplier tubes 142, it is desirable if the generation source of the sound wave is at the light guide 143 positioned in the middle. The features disclosed herein are not limited to the method by which the electric signal is input to the piezoelectric element 14a adhered to the light guide 143. For example, other methods by which the electric signal is input to a piezoelectric element adhered to the scintillator 141 or input to a piezoelectric element adhered to the photomultiplier tube 142 are also acceptable.

The sound wave detecting unit 27b detects the sound wave propagated within each of the detector modules 14. More specifically, the sound wave detecting unit 27b detects the sound wave (14d in FIG. 7) from the piezoelectric element 14b adhered to the predetermined one of the photomultiplier tubes 142 in the detector module 14. The features disclosed herein are not limited to the method by which the sound wave is detected from the piezoelectric element 14b adhered to the predetermined one of the photomultiplier tubes 142. For example, another method is acceptable by which, as shown in FIG. 8, the sound wave is detected from a piezoelectric element 14e that is adhered to the light guide 143 and is the same piezoelectric element as the one used for inputting the electric signal. Alternatively, another method is also acceptable by which the sound wave is detected from a piezoelectric element adhered to a predetermined one of the scintillators 141. In other words, as long as the sound wave is propagated within each of the detector modules 14, it is possible to detect the sound wave regardless of the position in which the piezoelectric element is adhered. Thus, it is possible to arbitrarily change the position and the number of piezoelectric elements.

The analyzing unit 27c analyzes the sound wave detected by the sound wave detecting unit 27b. More specifically, the analyzing unit 27c performs a frequency analysis using Fast Fourier Transform (FFT) or the like on the sound wave detected by the sound wave detecting unit 27b. The analyzing unit 27c detects whether an optical coupling detachment has occurred by looking for a frequency distribution specific to a surface having an optical coupling detachment as a result of the analysis. In this situation, for example, the analyzing unit 27c has stored in a storage unit in advance the "frequency distribution specific to a surface having an optical coupling detachment" identified in a separate experiment or the like. Further, by comparing the analysis result with the "frequency distribution specific to a surface having an optical coupling detachment" stored in the storage unit, the analyzing unit 27c looks for the frequency distribution specific to a surface having an optical coupling detachment and thus detects whether an optical coupling detachment has occurred.

As another example, the analyzing unit 27c may detect whether an optical coupling detachment has occurred by comparing a frequency distribution with another frequency distribution from a previous test. In this situation, for example, every time the analyzing unit 27c performs a test, the analyzing unit 27c stores the analysis result into a storage unit. Further, when having performed a new test, the analyzing unit 27c compares the analysis result of the new test with the analysis result stored in the storage unit, so as to detect whether an optical coupling detachment has occurred by, for example, detecting whether the analysis result exhibits a change that is equal to or larger than a predetermined threshold value.

The features disclosed herein are not limited to the methods described above. For example, the features disclosed herein include not only the method for detecting whether an optical coupling detachment has occurred, but also a method for identifying the position where an optical coupling detachment has occurred. In this situation, for example, the analyzing unit 27c calculates a correspondence relationship between the "position" where an optical coupling detachment has occurred and a "frequency characteristic of the sound wave" by performing a separate experiment or the like and stores the correspondence relationship into a storage unit in advance. Further, by referring to the correspondence relationship stored in the storage unit based on an analysis result and identifying the "position" stored in correspondence with the frequency characteristic indicated by the analysis result, the analyzing unit 27c identifies the position where the optical coupling detachment has occurred.

Alternatively, the method for identifying the position of an optical coupling detachment may be a method by which a plurality of piezoelectric elements are adhered to individual photomultiplier tubes 142 and/or individual scintillators 141, respectively. For example, as shown in FIG. 9, a piezoelectric element 14f may be adhered to the light guide 143, while piezoelectric elements 14g are adhered to the photomultiplier tubes 142, respectively. In this situation, the sound wave generating unit 27a inputs an electric signal to the piezoelectric element 14f adhered to the light guide 143, so that the sound wave detecting unit 27b detects the sound wave from each of the piezoelectric elements 14g adhered to the photomultiplier tubes 142.

Let us discuss a situation where, for example, an optical coupling detachment has occurred between the light guide 143 and a predetermined one of the photomultiplier tubes 142. In this situation, the sound wave detected from the piezoelectric element 14g adhered to the one of the photomultiplier tubes 142 having the optical coupling detachment is assumed to have a specific frequency distribution that is different from that of the sound wave detected from each of the piezoelectric elements 14g adhered to the other photomultiplier tubes 142. Accordingly, the analyzing unit 27c identifies the position of the optical coupling detachment (i.e., the photomultiplier tube 142 having the optical coupling detachment) by performing the frequency analysis on each of the plurality of sound waves detected by the sound wave detecting unit 27b and identifying the sound wave having the specific frequency distribution.

Returning to the description of FIG. 6, when the analyzing unit 27c has analyzed an occurrence of an optical coupling detachment, the notifying information outputting unit 27d outputs notifying information to notify the occurrence of the optical coupling detachment, to the display unit 22. Not only when an optical coupling detachment has occurred, but also when no optical coupling detachment has occurred, the notifying information outputting unit 27d may output notifying information so indicating to the display unit 22.

Advantageous Effects of the First Embodiment

As explained above, the PET apparatus 100 according to the first embodiment includes the optical coupling detachment testing unit 27. The optical coupling detachment testing unit 27 includes the sound wave generating unit 27a, the sound wave detecting unit 27b, and the analyzing unit 27c. The sound wave generating unit 27a inputs an electric signal to each of the detector modules 14 so as to generate a sound wave within the detector module 14. The sound wave detecting unit 27b detects the sound wave propagated within the detector module 14. The analyzing unit 27c analyzes the sound wave detected by the sound wave detecting unit 27b. As explained above, the PET apparatus 100 according to the first embodiment realizes the optical coupling detachment test by using the sound wave and is thus able to test for optical coupling detachments in a nondestructive manner.

In other words, according to this method, the electric signal is input so as to generate the sound wave and to detect the sound wave propagated within each of the detector modules 14, and based on the changes in the propagating characteristics of the sound wave, the occurrence and/or the position of the optical coupling detachment is identified. Thus, it is possible to perform the test in the dark and in a nondestructive manner because there is no need to disassemble the PET apparatus 100. In addition, as explained above, because the processes from the input of the electric signal through the analyzing process are performed automatically, the method is easy and does not take any trouble.

For this reason, the method makes it possible to, for example, easily perform a quality test during the manufacturing stage of the detector modules 14. Also, for example, after the PET apparatus 100 is installed, it is possible to perform the test on the PET apparatus 100 while in operation. Thus, for example, it is possible to incorporate the test as a check-up function during a maintenance inspection. Consequently, it is possible to perform the quality test frequently. In other words, it becomes possible to frequently test for optical defects, which are difficult to find, in a nondestructive and easy manner. Thus, the method is useful for improvements of quality and maintenance.

Further, as explained above, the optical coupling detachment testing unit 27 according to the first embodiment further includes the notifying information outputting unit 27d. When the analyzing unit 27c has analyzed an occurrence of an optical coupling detachment, the notifying information outputting unit 27d outputs the notifying information to notify the occurrence of the optical coupling detachment. With this arrangement, for example, a maintenance inspector is able to easily recognize the result of the optical coupling detachment test.

Further, as explained above, the sound wave generating unit 27a according to the first embodiment inputs the pulse signal as the electric signal, because pulse signal is suitable for generating a sound wave having a wide frequency band. With this arrangement, according to the first embodiment, it is possible to perform the optical coupling detachment test with a higher level of precision.

Furthermore, as explained above, in the first embodiment, by using the method by which, for example, the sound wave is generated at the light guide 143, it is possible to perform the optical coupling detachment test with a higher level of precision. Further, as explained above, in the first embodiment, by using the method by which, for example, the sound wave is detected for each of the scintillators 141 or for each of the photomultiplier tubes 142, it is possible to identify even the position where an optical coupling detachment has occurred. Alternatively, as explained above, in the first embodiment, it is also possible to use the method by which the position where an optical coupling detachment has occurred is detected, based on the correspondence relationship between the position where an optical coupling detachment has occurred and the frequency characteristic, by analyzing the frequency characteristic of the sound wave and referring to the storage unit.

Second Embodiment

Figure 10:
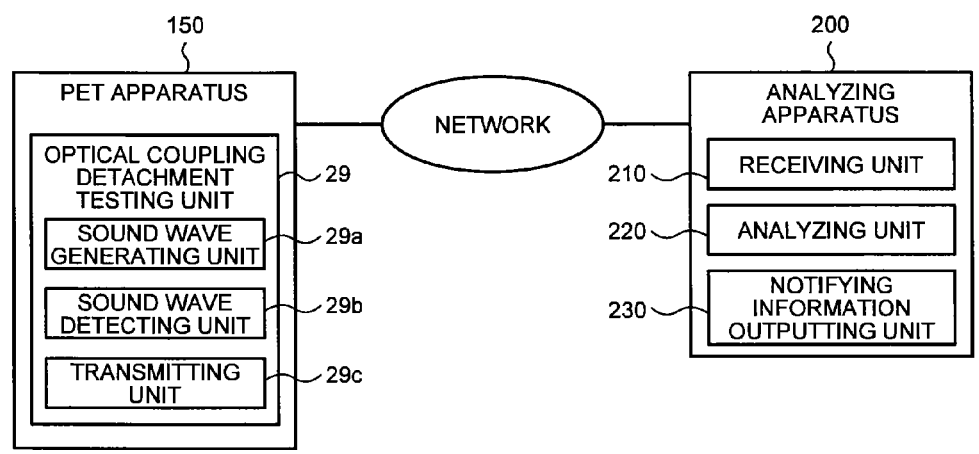
FIG. 10 is a drawing for explaining an analyzing system according to a second embodiment.

Next, an analyzing system according to the second embodiment will be explained, with reference to FIG. 10. As shown in FIG. 10, the analyzing system according to the second embodiment includes the PET apparatus 150 and the analyzing apparatus 200. The PET apparatus 100 according to the first embodiment is configured so that the optical coupling detachment testing unit 27 includes the analyzing unit 27c and the notifying information outputting unit 27d. In contrast, the PET apparatus 150 according to the second embodiment is configured so as to, instead of performing the analysis therein, transfer the information required to perform an analysis to the analyzing apparatus 200 that is connected thereto via a network. The analyzing apparatus 200 accordingly performs the analyzing process and a process to output notifying information. For example, it is possible to apply this configuration to a remote maintenance.

More specifically, as shown in FIG. 10, the PET apparatus 150 includes an optical coupling detachment testing unit 29, in place of the optical coupling detachment testing unit 27 included in the PET apparatus 100. The optical coupling detachment testing unit 29 includes, as shown in FIG. 10, a sound wave generating unit 29a, a sound wave detecting unit 29b, and a transmitting unit 29c. The PET apparatus 150 also includes the other functional units, like the PET apparatus 100 does.

Like the sound wave generating unit 27a according to the first embodiment, the sound wave generating unit 29a inputs an electric signal to each of the detector modules 14 so as to generate a sound wave in the detector module 14. Like the sound wave detecting unit 27b according to the first embodiment, the sound wave detecting unit 29b detects the sound wave propagated within each of the detector modules 14. The transmitting unit 29c transmits a signal related to the sound wave detected by the sound wave detecting unit 29b.

Further, the analyzing apparatus 200 includes, as shown in FIG. 10, a receiving unit 210, an analyzing unit 220, and a notifying information outputting unit 230. The receiving unit 210 receives, via the network, the signal related to the sound wave transmitted from the transmitting unit 29c. Like the analyzing unit 27c according to the first embodiment, the analyzing unit 220 analyzes the sound wave based on the signal related to the sound wave received by the receiving unit 210. Like the notifying information outputting unit 27d according to the first embodiment, when the analyzing unit 220 has analyzed an occurrence of an optical coupling detachment, the notifying information outputting unit 230 outputs notifying information to notify the occurrence of the optical coupling detachment.

The configuration of the analyzing system is not limited to the example shown in FIG. 10. Another arrangement is acceptable in which, for example, the processes up to the analyzing process is performed on the PET apparatus 150 side, whereas only the analysis result is transferred to the analyzing apparatus 200 side.

Third Embodiment

The features disclosed herein may be implemented in various modes other than the exemplary embodiments described above.

For example, in the first embodiment, although the exemplary configuration of the PET apparatus 100 is shown in FIG. 1, the features disclosed herein are not limited to this example. For instance, the count information acquiring unit 15 may be provided on the console device 20 side. On the contrary, the coincidence list generating unit 25 may be provided on the gantry device 10 side. Further, the various types of data stored in the data storage unit 24 may be provided on the gantry device 10 side or may be provided on the console device 20 side. The time period during which each of the pieces of data is stored in the PET apparatus 100 can also be arbitrarily determined.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine imaging apparatus comprising:
a detector configured to detect radiation emitted from a subject;
a sound wave generating unit configured to input an electric signal to the detector and to generate a sound wave within the detector;
a sound wave detecting unit configured to detect the sound wave propagated within the detector; and
an analyzing unit configured to analyze the sound wave detected by the sound wave detecting unit.

2. The nuclear medicine imaging apparatus according to claim 1, further comprising: a notifying information outputting unit configured to, when the analyzing unit has analyzed an occurrence of an optical coupling detachment, output notifying information to notify the occurrence of the optical coupling detachment.

3. The nuclear medicine imaging apparatus according to claim 1, wherein the sound wave generating unit inputs a pulse signal as the electric signal.

4. The nuclear medicine imaging apparatus according to claim 1, wherein
the detector includes: a scintillator configured to convert the radiation emitted from the subject into scintillation light; a photomultiplier tube configured to multiply the scintillation light and to convert the multiplied scintillation light into an electric signal; and a light guide configured to output the scintillation light having been output from the scintillator to the photomultiplier tube, and
the sound wave generating unit generates the sound wave at the light guide.

5. The nuclear medicine imaging apparatus according to claim 1, wherein
the detector includes: one or more scintillators each of which is configured to convert the radiation emitted from the subject into scintillation light; one or more photomultiplier tubes each of which is configured to multiply the scintillation light and to convert the multiplied scintillation light into an electric signal; and a light guide configured to output the scintillation light having been output from the one or more scintillators to the one or more photomultiplier tubes, the sound wave detecting unit detects the sound wave for each of the one or more scintillators and/or for each of the one or more photomultiplier tubes, and the analyzing unit identifies a position where an optical coupling detachment has occurred by analyzing the sound wave detected by the sound wave detecting unit for each of the one or more scintillators and/or for each of the one or more photomultiplier tubes.

6. The nuclear medicine imaging apparatus according to claim 1, further comprising:

a storage unit configured to store therein a correspondence relationship between a position where an optical coupling detachment occurs and a frequency characteristic of the sound wave analyzed by the analyzing unit, wherein the analyzing unit analyzes a frequency characteristic of the sound wave detected by the sound wave detecting unit, refers to the storage unit, and identifies a position where an optical coupling detachment has occurred based on the correspondence relationship with the frequency characteristic.

7. An analyzing system comprising:

a nuclear medicine imaging apparatus that includes:

a detector configured to detect radiation emitted from a subject;

a sound wave generating unit configured to input an electric signal to the detector and to generate a sound wave within the detector;

a sound wave detecting unit configured to detect the sound wave propagated within the detector; and a transmitting unit configured to transmit a signal related to the sound wave detected by the sound wave detecting unit;

a receiving unit configured to receive, via a network, the signal related to the sound wave transmitted from the transmitting unit; and an analyzing unit configured to analyze the sound wave based on the received signal related to the sound wave.

* * * * *